(12) United States Patent
He et al.

(10) Patent No.: US 10,584,362 B2
(45) Date of Patent: Mar. 10, 2020

(54) **METHODS FOR SIMULTANEOUSLY SYNTHESIZING A BIOLOGICAL FLOCCULANT WITH TWO DIFFERENT COMPONENTS BY USING *BACILLUS LICHENIFORMIS***

(71) Applicant: Xiamen University, Xiamen, Fujian Province (CN)

(72) Inventors: Ning He, Xiamen (CN); Haosheng Yao, Xiamen (CN); Yu Liu, Xiamen (CN); Wencheng Yu, Xiamen (CN); Shan Yan, Xiamen (CN); Yuanpeng Wang, Xiamen (CN); Qingbiao Li, Xiamen (CN)

(73) Assignee: Xiamen University, Xiamen, Fujian Province (CN)

( * ) Notice: Subject to any disclaimer, the term of this patent is extended or adjusted under 35 U.S.C. 154(b) by 18 days.

(21) Appl. No.: 15/303,944

(22) PCT Filed: Jul. 30, 2014

(86) PCT No.: PCT/CN2014/083293
§ 371 (c)(1),
(2) Date: Oct. 13, 2016

(87) PCT Pub. No.: WO2015/158061
PCT Pub. Date: Oct. 22, 2015

(65) Prior Publication Data
US 2017/0029855 A1 Feb. 2, 2017

(30) Foreign Application Priority Data
Apr. 14, 2014 (CN) .......................... 2014 1 0148579

(51) Int. Cl.
*C12P 19/04* (2006.01)
*C12N 1/20* (2006.01)
*C12P 21/02* (2006.01)
*C07K 14/32* (2006.01)

(52) U.S. Cl.
CPC .............. *C12P 19/04* (2013.01); *C07K 14/32* (2013.01); *C12N 1/20* (2013.01); *C12P 21/02* (2013.01)

(58) Field of Classification Search
None
See application file for complete search history.

(56) References Cited

U.S. PATENT DOCUMENTS

2003/0124674 A1* 7/2003 Lee .................... C12P 21/02 435/69.1

FOREIGN PATENT DOCUMENTS

| CN | 101503709 | * | 8/2009 |
| CN | 101503709 A | | 8/2009 |
| CN | 101503709 A | * | 7/2013 |
| CN | 103194499 A | | 7/2013 |
| CN | 103525879 A | | 1/2014 |
| CN | 103667412 A | | 3/2014 |
| CN | 103937838 A | | 7/2014 |

OTHER PUBLICATIONS

Xiong et al. Production and Characterization of a Novel Bioflocculant from Bacillus licheniformis., Appl and Environ Microbiol (2010), 76(9): 2778-2782.*
Shih et al. Application of statistical experimental methods to optimize production of poly(γ-glutamic acid) by Bacillus licheniformis CCRC 12826., Enzyme and Microbial Technology 31 (2002): 213-220).*
English Translation of the PCT International Search Report dated Dec. 22, 2014 for International Application No. PCT/CN2014/083293 (4 pages).
PCT Written Opinion of the International Searching Authority dated Dec. 22, 2014 for International Application No. PCT/CN2014/083293 (4 pages).
Kang J.X.,Bai Y.S., Study and Application of Water Treatment Flocculants[J], Journal of Huazhong University of Science and Technology, 2004,6: 23-25. (English Abstract).
Nakamura J, Miyashiro S, Hirose Y. Screening, isolation, and some properties of microbial cell flocculants[J]. Agricultural and Biological Chemistry, 1976, 40(2): 377-383.
Takagi H, Kadowaki K. Purification and chemical properties of a flocculant produced by Paecilomyces[J]. Agricultural and biological chemistry, 1985, 49(11): 3159-3164.
Napoli C, Dazzo F, Hubbell D. Production of cellulose microfibrils by Rhizobium[J]. Applied microbiology, 1975, 30(1): 123-131.
Zhang J, Wang R, Jiang P, et al. Production of an exopolysaccharide bioflocculant by Sorangium cellulosum[J]. Letters in applied microbiology, 2002, 34(3): 178-181.
Toeda K, Kurane R. Microbial flocculant from Alcaligenes cupidus KT201[J]. Agricultural and Biological Chemistry, 1991, 55(11): 2793-2799.

(Continued)

*Primary Examiner* — Iqbal H Chowdhury
(74) *Attorney, Agent, or Firm* — Fitch, Even, Tabin & Flannery, LLP

(57) ABSTRACT

The present application provides a method for simultaneously synthesizing a biological flocculant with polysaccharide and γ-PGA as the active components by using *Bacillus licheniformis*. *Bacillus licheniformis* is inoculated to a slant culture medium to be cultured; a single colony on a fresh plate is inoculated to a seed culture medium to be cultured; and a seed fermentation broth is inoculated to a fermentation culture medium to be cultured, and then the biological flocculant having two different components is obtained. The flocculant synthesized in the present invention is high in activity and good in thermal stability; and especially, the flocculation effect of polysaccharide is relatively superior under acidic and neutral conditions, and the flocculation activity of γ-PGA is relatively higher under neutral and alkaline environments, which can satisfy a relatively large pH application range.

5 Claims, 2 Drawing Sheets

(56) References Cited

OTHER PUBLICATIONS

Suh H H, Kwon G S, Lee C H, et al. Characterization of bioflocculant produced by *Bacillus* sp. DP-152[J]. Journal of Fermentation and Bioengineering, 1997, 84(2): 108-112.

Deng S, Bai R, Hu X, et al. Characteristics of a bioflocculant produced by *Bacillus mucilaginosus* and its use in starch wastewater treatment[J]. Applied microbiology and biotechnology, 2003, 60(5): 588-593.

He N, Li Y, Chen J, et al. Identification of a novel bioflocculant from a newly isolated Corynebacterium glutamicum[J]. Biochemical Engineering Journal, 2002, 11(2): 137-148.

He N, Li Y, Chen J. Production of a novel polygalacturonic acid bioflocculant REA-11 by Corynebacterium glutamicum[J]. Bioresource Technology, 2004, 94(1): 99-105.

Salehizadeh H, Vossoughi M, Alemzadeh I. Some investigations on bioflocculant producing bacteria[J]. Biochemical engineering journal, 2000, 5(1): 39-44.

Deng S, Yu G, Ting Y P. Production of a bioflocculant by Aspergillus parasiticus and its application in dye removal[J]. Colloids and surfaces B: Biointerfaces, 2005, 44(4): 179-186.

Xia S, Zhang Z, Wang X, et al. Production and characterization of a bioflocculant by Proteus mirabilis TJ-1[J]. Bioresource technology, 2008, 99(14): 6520-6527.

Zheng Y, Ye Z L, Fang X L, et al. Production and characteristics of a bioflocculant produced by *Bacillus* sp. F19[J]. Bioresource Technology, 2008, 99(16): 7686-7691.

Li Z, Zhong S, Lei H, et al. Production of a novel bioflocculant by Bacilluslicheniformis X14 and its application to low temperature drinking water treatment[J]. Bioresource Technology, 2009, 100(14): 3650-3656.

Aljuboori A H R, Idris A, Abdullah N, et al. Production and characterization of a bioflocculant produced by Aspergillus flavus[J]. Bioresource technology, 2013, 127: 489-493.

Zhao H, Liu H, Zhou J. Characterization of a bioflocculant MBF-5 by Klebsiella pneumoniae and its application in Acanthamoeba cysts remoyal[J]. Bioresource technology, 2013, 137: 226-232.

Wang L, Ma F, Lee J, et al. Bioflocculants from hydrolysates of corn stover using isolated strain Ochrobactium ciceri W2[J]. Bioresource technology, 2013, 145: 259-263.

Nakamura J, Miyashiro S, Hirose Y. Purification and chemical analysis of microbial cell flocculant produced by Aspergillus sojae AJ7002[J]. Agricultural and Biological Chemistry, 1976, 40(3): 619-624.

Takeda M, Kurane R, Koizumi J, et al. A protein bioflocculant produced by Rhodococcus erythropolis[J]. Agricultural and Biological Chemistry, 1991, 55(10): 2663-2664.

Ashiuchi M, Misono H, Biochemistry and molecular genetics of poly-y-glutamate synthesis[J], Applied Microbiology and Biotechnology, 2002, 59(1): 9-14.

Shih I L, Van Y T, Yeh L C, et al. Production of a biopolymer flocculant from Bacillus licheniformis and its flocculation properties[J]. Bioresource technology, 2001, 78(3): 267-272.

Yokoi H, Natsuda O, Hirose J, et al. Characteristics of a biopolymer flocculant produced by *Bacillus* sp. PY-90[J]. Journal of Fermentation and Bioengineering, 1995, 79(4): 378-380.

Yokoi H, Arima T, Hirose J, et al. Flocculation properties of poly (γ-glutamic acid) produced by *Bacillus subtilis*[J]. Journal of Fermentation and Bioengineering, 1996, 82(1): 84-87.

Gao Q, Zhu X H, Mu J, et al. Using Ruditapes philippinarum conglutination mud to produce bioflocculant and its applications in wastewater treatment[J]. Bioresource technology, 2009, 100(21): 4996-5001.

Bajaj I B, Singhal R S. Flocculation properties of poly (γ-glutamic acid) produced from *Bacillus subtilis* isolate[J]. Food and Bioprocess Technology, 2011, 4(5): 745-752.

Zhao C, Zhang Y, Wei X, et al. Production of ultra-high molecular weight poly-γ-glutamic acid with Bacillus licheniformis P-104 and characterization of its flocculation properties[J]. Applied biochemistry and biotechnology, 2013, 170(3): 562-572.

Chen, Zhen, et al., "Identification of Key Genes Involved in Polysaccharide Bioflocculant Synthesis in Bacillus licheniformis," Biotechnology and Bioengineering, vol. 114, No. 3, Mar. 2017, pp. 645-655.

Yu, Wencheng, et al., "Effect of glucose on poly-γ-glutamic acid metabolism in Bacillus licheniformis," Microbial Cell Factories, 16:22, 2017, 10 pages.

* cited by examiner

METHODS FOR SIMULTANEOUSLY SYNTHESIZING A BIOLOGICAL FLOCCULANT WITH TWO DIFFERENT COMPONENTS BY USING *BACILLUS LICHENIFORMIS*

CROSS-REFERENCE TO RELATED APPLICATIONS

This application is a U.S. national phase application filed under 35 U.S.C. § 371 of International Application Number PCT/CN2014/083293, filed Jul. 30, 2014, designating the United States, which claims priority from Chinese Application Number CN 201410148579.6, filed Apr. 14, 2014.

FIELD OF THE INVENTION

The present invention relates to biological flocculants, and especially relates to methods for simultaneously synthesizing a biological flocculant with two different components by using *Bacillus licheniformis*.

DESCRIPTION OF THE PRIOR ART

Biological flocculants are the secondary metabolic products of microorganisms or chemically modified natural organic polymers having flocculation activity, which are a type of novel flocculants obtained through the methods of culturing microorganisms by using biotechnology. The chemical components thereof are mainly the substances of glycoproteins, polysacharides, proteins, celluloses and nucleic acids and the like, the molecular weights are about over hundreds of thousands (Journal of Huazhong University of Science and Technology Urban Science Edition, 2004, 6: 23-25). Flocculent microorganisms can enable the dispersed particles, comprising the bacterial cells per se, to be adhered to one another, and can enable colloids to be destabilized, forming flocculent precipitate and thereby be separated from the reaction system.

The flocculation phenomenon of microorganisms was earliest discovered in wine industry. A French Louis Pasteur discovered that the Saccharomycetes Levure casseeuse has flocculation capability at anaphase of fermentation in 1876. In 1950s, a Japanese scholar discovered that microorganism culture liquids have flocculation action. In 1976, J. Nakamura et al. carried out special research on the microorganisms that can produce flocculation effect, booming the research wave on microbial flocculants (Agric Biol Chem, 1976, 40(2): 377-383). In water treatment, the traditional chemical flocculants not only have the characteristics of large in the amount of addition and large in sludge yield, but the produced chemical sludge is not easily degraded by organisms, which is potentially harmful to human health and water environmental ecology when discharged into water body. Therefore, chemical flocculants are limited in application scope and using conditions, and the prospect is not optimistic. Biological flocculants not only have flocculation properties that general flocculants have, but also have advantages of low dosage, good flocculation effect, easy separation of floc, easy biodegradation, free from secondary pollution, no harm to human health, broad application range and the like that general flocculants do not have. Therefore, the research and application of biological flocculants have become hot point and key point for developing novel and efficient flocculants.

According to chemical components, biological flocculants can be classified into the types of polypeptides or proteins, polysaccharides, lipids and DNA and the like. The presently common ones therein are polysaccharides and polypeptides or proteins.

Many types of biological flocculants that have been presently identified belong to polysaccharides substance. The PF-101 flocculant generated by *Paecilomyces* sp. I-1 is mucopolysaccharide formed by aminogalactose by means of α-1,4-glycosidic bond linkage (Agricultural and Biological Chemistry, 1985, 49(11): 3159-3164). The major component of the flocculants generated by *Rhizobium* sp. is cellulose, which is generally attached to the cell wall of the producing bacterium, and directly cause flocculation precipitate of bacterial cells (Applied Microbiology, 1975, 30(1): 123-131).

*Sorangium cellulosum* NUST06 is cultured under the condition of 30° C. and pH 7.5 for 36 h in the culture medium (m/v): starch 30 g $L^{-1}$, glucose 2 g $L^{-1}$, $K_2HPO_4$ 0.2%, $CaCl_2$ 0.01%, $MgSO_4$ 0.03%, $FeCl_2$ 0.001%, $KNO_3$ 0.3%. The yield of polysaccharides flocculant can reach 17.5 g $L^{-1}$, accounting for 58.5% of the total product. Wherein each monomer of glucose, manose and glucuronic acid accounts for a ratio of 51.3%, 39.2%, 19.5%, respectively. Maximum flocculation ratio can reach 99.5% (Letters in Applied Microbiology 2002, 34: 178-181).

Kazuki TOEDA uses *Alcaligenes cupidus* KT201 to be cultured under the condition of 30° C. for 6~8 days in the culture medium (m/v): sucrose 2%, $(NH_4)_2SO_4$ 0.01%, $CaCl_2.2H_2O$ 0.002%, $MgSO_4.7H_2O$ 0.02%, $NaCl_2$ 0.01%, $FeSO_4.7H_2O$ 0.001%, $KH_2PO_4$ 0.16% and yeast extract 0.02%. Each monomer of glucose, galactose, glucuronic acid and acetic acid in the generated polysaccharides flocculant accounts for the ratio of 42.57%, 36.38%, 8.52% and 10.3%, respectively. The maximum flocculation activity is about 10.8 OD-1 (Agricultural and Biological Chemistry, 1991, 55(11): 2793-2799).

*Bacillus* sp. DP-152 is cultured under the condition of 30° C. and pH 7.0 for 3 days in the culture medium (g $L^{-1}$): glucose 40, $NH_4NO_3$ 1.0, $K_2HPO_4$ 0.3, $KH_2PO_4$ 0.3, $MgSO_4.7H_2O$ 0.1, $MnSO_4.4H_2O$ 0.1, NaCl 0.05, $CaCO_3$ 0.4, yeast extract 0.1, soy peptone 0.1 and tryptone 0.1. The ratio of the monomers glucose, mannose, galactose and trehalose in the generated polysaccharides is 8:4:2:1. The maximum flocculation activity is about 43 $OD^{-1}$ (Journal of Fermentation and Bioengineering, 1997, 84(2): 108-112).

S. B. Deng et al. uses *Bacillus mucilaginosus* to be cultured under the optimal condition of 30° C. and pH 8.0 for 72 h in the culture medium (g $L^{-1}$): soluble starch 1.5, $K_2HPO_4$ 0.6, yeast extract 0.02, $MgSO_4.7H_2O$ 0.02, NaCl 0.01. The principal component of the generated biological flocculant MBFA9 is polysaccharides, wherein glycuronic acid, neutral saccharide and aminosaccharide account for a ratio of 19.1%, 47.4% and 2.7%, respectively. The maximum flocculation ratio of treating Kaolin is 99.6% (Appl Microbiol Biotechnol, 2003, 60:588-593).

*Corynebacterium glutamicum* CCTCC M201005 is cultured under the condition of 28° C. and pH 7.8 for 48 h in the culture medium ($L^{-1}$): sucrose 17 g, comsteep liquor 5 ml, urea 0.45 g, $KH_2PO_4$ 0.1 g, NaCl 0.1 g and $MgSO_4.7H_2O$ 0.1 g. The generated biological flocculant REA-11 is mainly composed of galacturonic acid (Biochemical Engineering Journal, 2002, 11: 137-148), and flocculation activity can reach 520 U/mL (Bioresource Technology 2004, 94: 99-105).

H. Salehizadeh uses *Bacillus* sp. As-101 to be cultured under the condition of 30° C. for 10~15 h in the culture medium (m/v): peptone 0.5%, $(NH_4)_2SO_4$ 0.2%, yeast powder 0.1%, $CaCl_2.2H_2O$ 0.07%, $MgSO_4.7H_2O$ 0.02%, $NaCl_2$ 0.01%, K$_2$HPO$_4$ 0.1%, glucose 0.1% and agar 0.3%. 83% of the generated biological flocculant is polysaccharides, others are proteins. The monomers composing the polysaccharides are glucose, galactose, mannose, glycuronic acid, pyruvic acid and acetic acid, respectively. The maximum flocculation activity is 27 OD$^{-1}$. After treating at 100° C. for 15 minutes, flocculation activity decreased 50% (Biochemical Engineering Journal 2000, 5: 39-44).

*Aspergillus parasiticus* is cultured under the condition of 28° C. at initial pH 5.0~6.0 for 3 days in the culture medium (L$^{-1}$): sucrose 30, NaNO$_3$ 3.0, MgSO$_4$.7H$_2$O 0.5, KCl 0.5, FeSO$_4$ 0.01, and KH$_2$PO$_4$ 1.0. The obtained biological flocculant contains 76.3% of polysaccharides therein. When kaolin is treated, the maximum flocculation ratio can reach 98.1%, the decolourization ratio of printing and dyeing wastewater is also higher than 96% (Colloids and Surfaces B: Biointerfaces 2005, 44: 179-186).

*Proteus mirabilis* TJ-1 is cultured under the condition of 30° C. and pH 7.0 for 48 h in the culture medium (g L$^{-1}$): glucose 10, tryptone 1, K$_2$HPO$_4$ 5, KH$_2$PO$_4$ 2, MgSO$_4$.7H$_2$O 0.3. 63.1% (w/w) of the generated biological flocculant is polysaccharides. Wherein the ratio of neutral saccharide, glycuronic acid and aminosaccharide is 8.2:5.3:1. The maximum flocculation ratio is 93.13% (Bioresource Technology 2008, 99: 6520-6527).

*Bacillus* sp. F19 is cultured under the condition of 30° C. and pH 7.0 for 48 h in the culture medium (g L$^{-1}$): glucose 10, yeast extract 0.5, (NH$_4$)$_2$SO$_4$ 0.2, K$_2$HPO$_4$ 5, KH$_2$PO$_4$ 2, urea 0.5, and NaCl 0.1. The generated biological flocculant MBFF19 is glycoprotein derivatives, wherein the ratio (w/w) of neutral saccharide, glycuronic acid, amino saccharide and protein is 3.6%, 37.0%, 0.5% and 16.4%, respectively, while the ratio of the two types of neutral saccharides is 1.2:1. The maximum flocculation ratio of treating kaolin is 97% (Bioresource Technology 2008, 99: 7686-7691).

*Bacillus licheniformis* X14 is cultured under the optimal condition of 37° C. and pH 8.0 for 48 h in the culture medium (g L$^{-1}$): glucose 20, yeast extract 0.5, urea 0.5, (NH$_4$)$_2$SO$_4$ 0.2, MgSO$_4$.7H$_2$O 0.2, K$_2$HPO$_4$ 5, KH$_2$PO$_4$ 2, and NaCl 0.1. The generated biological flocculant ZS-7 contains 91.5% (w/w) of polysaccharides, wherein the ratios of glycuronic acid, pyruvic acid and acetic acid to total product are 16.4%, 7.1% and 0.5%. The maximum flocculation ratio of treating kaolin is 99.2%, and the removal rate of COD$_{Mn}$ of low temperature drinking water and turbidity is 61.2% and 95.6%, respectively (Bioresource Technology 2009, 100: 3650-3656).

*Aspergillus flavus* S44-1 is cultured under the condition of 30° C. and pH 6.0 for 3 days in the culture medium (g L$^{-1}$): sucrose 30, tryptone 3.0, MgSO$_4$.7H$_2$O 0.5, KCl 0.5, FeSO$_4$ 0.01, KH$_2$PO$_4$ 1.0. The generated biological flocculant IH-7 contains 69.7% (w/w) polysaccharides, wherein the ratios of neutral saccharide, glycuronic acid and aminosaccharide to total product are 40%, 2.48% and 1.8%. The components of neutral saccharides are sucrose, lactose, glucose, xylose, galactose, mannose and fructose, and the ratio is 2.4:4.4:4.1:5.8:9.9:0.8:3.1. The maximum flocculation ratio of treating kaolin can reach over 95% (Bioresource Technology 2013, 127:489-493).

*Klebsiella pneumoniae* LZ-5 is cultured under the condition of 30° C. and pH 8.0 for 3 days in the culture medium (g L$^{-1}$): glucose 20, yeast extract 0.5, urea 0.5, (NH$_4$)$_2$SO$_4$ 0.2, K$_2$HPO$_4$ 5, KH$_2$PO$_4$ 2, NaCl 0.1. The generated biological flocculant MBF-5 contains 96.8% (w/w) of polysaccharides and 2.1% of proteins, wherein the ratios of neutral saccharide, glycuronic acid and amino saccharide to total product are 50%, 3.44% and 4.2%. The components of neutral saccharides are glucose, mannose, galactose, and glucosamine, and the ratio is 4.1:1.3:2.7:3.2. The flocculation ratio of treating kaolin can reach over 98% (Bioresource Technology 2013, 137: 226-232).

*Ochrobactrum ciceri* W2 is cultured under the optimal condition of 30° C. and pH 7.5 for 16 h in the culture medium (g L$^{-1}$): glucose or fructose 10, yeast extract 0.5, urea 0.5, (NH$_4$)$_2$SO$_4$ 0.2, MgSO$_4$ 0.2, K$_2$HPO$_4$ 5, KH$_2$PO$_4$ 2, NaCl 0.1. The produced biological flocculant comprising polysaccharides and proteins can reach maximum yield of 3.8 g L$^{-1}$. The flocculation ratio of treating kaolin reaches maximum at 30 h, which is 92% (Bioresource Technology, doi: 10.1016/j.biortech.2012.11.020).

Yumiao Xiong et al use *Bacillus licheniformis* CGMCC 2876 to be shaking cultured under the condition of pH7.2, 200 rpm, and 37° C. for 48 h in the culture medium (g L$^{-1}$): sucrose 15, urea 1, yeast extract 1, KH$_2$PO$_4$ 5, MnSO$_4$.H$_2$O 0.05, and NaCl 2. The synthesized biological flocculant contains 89% of polysaccharides, and the flocculation activity reaches 750 U mL$^{-1}$ (Patent number: ZL 200910111262).

The principal active components of flocculant synthesized by *Asp. sojae* AJ7002 are proteins and hexosamines (Agricultural and Biological Chemistry, 1976, 40: 619-624); biological flocculant NOC-1 is also a type of protein, and the protein molecule comprises relatively more hydrophobic amino acids therein (Agricultural and Biological Chemistry, 1991, 55: 2663-2664). Alanine, glutamic acid, glycine and aspartic acid etc are contained, and the maximum molecular weight is 750,000. γ-polyglutamic acid (γ-PGA) is a type of polypeptide molecule polymerized from L-glutamic acid and D-glutamic acid monomers through amide linkage (Applied Microbiology and Biotechnology, 2002, 59(1): 9-14), containing lots of free carboxyl groups in the molecule, and is a biodegradable novel biological flocculant.

Shih et al use *Bacillus licheniformis* CCRC 12826 to be fermented under the condition of 37° C. and pH 6.5 for 96 h in the culture medium (g L$^{-1}$): glutamic acid 20, citric acid 12, glycerol 120, NH$_4$Cl 7, MgSO$_4$.7H$_2$O 0.5, FeCl$_3$.H$_2$O 0.004, K$_2$HPO$_4$ 0.5 and CaCl$_2$ 0.15, then the viscosity of the obtained γ-PGA is 17 cp, and the flocculation ratio of treating Ca(OH)$_2$ solution reaches 11 OD$^{-1}$ (Bioresoure Technology 2001, 78: 267-372).

*Bacillus* sp. PY-90 is fermented under the condition of 30° C. for 48 h in the culture medium (m/v): glucose 2.0%, K$_2$HPO$_4$ 0.2%, MgSO$_4$.7H$_2$O 0.05%, multi-peptone 1.0%, yeast extract 0.05% and agar 2.0%. The flocculation activity of the obtained γ-PGA in kaolin solution is 15 OD$^{-1}$. When the temperature reaches 100° C., the flocculation activity begins to decrease (Journal of Fermentation and Bioengineering 1995, 79: 378-380).

*Bacillus subtilis* IFO 3335 is fermented under the condition of 30° C. for 72 h in the culture medium (m/v): glutamic acid 3.0%, NH$_4$Cl 1.0%, glucose 1.0%, K$_2$HPO$_4$ 0.2%, yeast extract 0.2% and MgSO$_4$.7H$_2$O 0.2%. The flocculation activity of the obtained γ-PGA in acidic clay is 14 OD$^{-1}$ (Journal of Fermentation and Bioengineering 1996, 82: 84-87).

γ-PGA producing bacterium *Ruditapes philippinarum* ZHT4-13 is fermented under the condition of 30° C. and pH 8.0 for 4 days in the culture medium (g L$^{-1}$): glucose 20, (NH$_4$)$_2$SO$_4$ 0.2, urea 0.5, yeast extract 0.5, MgSO$_4$.7H$_2$O 0.2, KH$_2$PO$_4$ 2.0 and K$_2$HPO$_4$ 5.0, then the flocculation ratio of treating kaolin reaches 86.22% (Bioresource Technology 2009, 100: 4996-5001).

γ-PGA producing bacterium *Bacillus subtilis* R 23 is fermented under the condition of 37±2° C. for 48 h in the culture medium (g L$^{-1}$): glucose 52.5, citric acid 15.5, NaCl 20, $(NH_4)_2SO_4$ 4.75, L-glutamic acid 20, KCl 0.66, $K_2HPO_4$ 1, $MgSO_4 \cdot 7H_2O$ 6.8, $CaCl_2 \cdot 2H_2O$ 0.18, $NaHCO_3$ 0.18, $MgCl_2 \cdot 6H_2O$ 4.7, α-ketoglutaric acid 5 mM and $MnSO_4 \cdot 7H_2O$ 0.05, then the flocculation ratio of treating kaolin reaches 30.32 $OD^{-1}$ (Food and Bioprocess Technology 2011, 4: 745-752).

*Bacillus licheniformis* P-104 is cultured under the condition of 37° C. and pH 7.2 for 36 h in the culture medium (g $L^{-1}$): sodium glutamic acid 50, glucose 50, sodium citric acid 12, $NH_4Cl$ 7, $K_2HPO_4$ 0.5, $MgSO_4 \cdot 7H_2O$ 0.5, $CaCl_2 \cdot 2H_2O$ 0.15 and $MnSO_4 \cdot 7H_2O$ 0.104. The yield of the obtained γ-PGA is 41.6 g $L^{-1}$, and the productive rate is 1.07 g $L^{-1} 11^{-1}$. After being diluted 20 times, the flocculation activity of the culture solution can reach 46.66±2.89 $OD^{-1}$ (Appl Biochem Biotechnol 2013, 170:562-572).

Shan Yan et al. use *Bacillus licheniformis* CGMCC 2876 to be cultured under the condition of pH 7.2, 200 rpm and 37° C. for 20 h in the culture medium (g $L^{-1}$): trisodium citrate 20, glycerol 20, $NH_4Cl$ 9, sodium glutamic acid 10, $MgSO_4 \cdot 7H_2O$ 0.5, $K_2HPO_4$ 0.5. The yield of the obtained flocculant is 21.8 g $L^{-1}$, wherein the content of γ-PGA is 94.3%, and the flocculation activity reaches 11679 U $mL^{-1}$ (see Chinese Patent CN103194499A).

At present, although there have been many detailed researches on using microbiological methods to produce biological flocculants taking polysaccharides as the principal component or γ-PGA as the principal component, there has been rare report on methods for simultaneously synthesizing a biological flocculant taking both polysaccharides and γ-PGA as the active components by using some single bacterial strain under one culture condition.

SUMMARY OF THE INVENTION

The purpose of the present invention lies in providing a method for simultaneously synthesizing biological flocculants with two different components by using *Bacillus licheniformis*, specific to the problems present in the current production of biological flocculants that the cost of raw materials is high, fermentation period is long, flocculation activity is low, thermal stability is inferior, it is difficult to promote and the like.

The microorganism adopted in the present invention is *Bacillus licheniformis*, the microorganism has been deposited in the Center for General Microorganism of the Administration Committee of the China Microbiological Culture Collection on Jan. 14, 2009, and the depository serial number of depository center is CGMCC No. 2876 (see Chinese Patent CN101503709).

The specific steps of the present application are as follows:

1) bacterial strain activation: *Bacillus licheniformis* is inoculated to a slant medium to be cultured;
2) preparation of seed: a single colony on a fresh plate is inoculated to a seed culture medium to be cultured;
3) fermentation culture: a seed fermentation broth is inoculated to a fermentation culture medium to be cultured, and then the biological flocculant with two different components is obtained.

In step 1), the composition of the slant culture medium can be (g $L^{-1}$): yeast extract 2, beef extract 2, tryptone 5, glucose 15, $FeSO_4$ trace, agar 18, and pH 5~7.5; the culture condition can be cultured at 37° C. and 200 r/min for 12~18 h.

In step 2), the composition of the seed culture medium can be (g $L^{-1}$): glucose 10, yeast extract 0.5, urea 0.5, $K_2HPO_4$ 0.1, $KH_2PO_4$ 0.1, NaCl 0.1, and $MgSO_4 \cdot 7H_2O$ 0.2; the culture condition can be: temperature 37° C., the shaking speed of shaker 200 r/min, and culture time 16 h.

In step 3), the inoculation amount of the inoculation can be 3%; the composition of the fermentation culture medium can be (g $L^{-1}$): glucose 5~15, trisodium citrate 10~15, glycerol 10~15, urea 1~3, yeast extract 0.5~1, $NH_4Cl$ 2~6, sodium glutamate 2~6, $MgSO_4$ 0.3~0.5, $K_2HPO_4$ 0.5~2, $KH_2PO_4$ 1~5, NaCl 1~3 and pH 5~7.5; the culture condition can be cultured in shaking flask under the condition of 200 r/min at the temperature of 37° C. with liquid loading volume of 50 mL/250 mL, and fermentation time of 16~48 h, the obtained biological flocculant takes polysaccharides and γ-PGA as the active components.

The present invention synthesizes a biological flocculant simultaneously taking polysaccharides and γ-PGA as the active components under one culture condition by using *Bacillus licheniformis*. The advantages of this method are that the cost of raw materials is relatively low, fermentation period is short, the synthesized flocculant is high in activity, thermal stability is superior; especially, the flocculation effect of polysaccharide is relatively superior under acidic and neutral conditions, and the flocculation activity of γ-PGA is relatively higher under neutral and alkaline environments. Synthesizing a biological flocculant simultaneously taking polysaccharides and γ-PGA as the active components can satisfy a larger pH application range, of which the industrial application potential is large.

DETAILED DESCRIPTION OF THE PREFERRED EMBODIMENTS

The present invention will be further illustrated over the following Examples in combination with the figures so as to provide basis for better understanding the present invention.

Example 1

Figure 1:
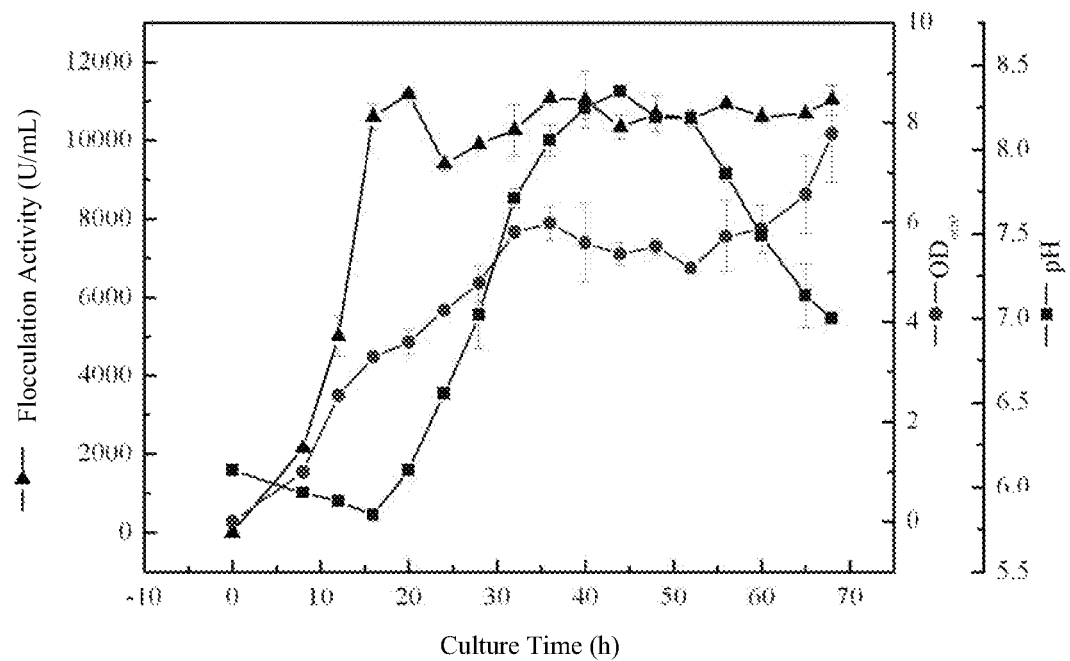
FIG. 1 is the fermentation curve of *Bacillus licheniformis* CGMCC 2876.

The composition of fermentation culture medium (g $L^{-1}$): glucose 12, trisodium citrate 15, glycerol 15, urea 2.5, yeast extract 0.6, $NH_4Cl$ 5, sodium glutamate 5, $MgSO_4$ 0.5, $K_2HPO_4$ 0.5, $KH_2PO_4$ 5 and NaCl 2. When fermentation time is 20 h, flocculation activity reaches 11179 U $mL^{-1}$ (see FIG. 1).

Example 2

The culture condition is the same as that of Example 1, the effect of the composition of fermentation culture medium on flocculant synthesis is investigated. The distinction lies in that the concentration of glucose in the fermentation culture medium used is 5 g $L^{-1}$.

Example 3

The culture condition is the same as that of Example 1, the effect of the composition of fermentation culture medium on flocculant synthesis is investigated. The distinction lies in that the concentration of glucose in the fermentation culture medium used is 15 g $L^{-1}$.

Example 4

The culture condition is the same as that of Example 1, the effect of the composition of fermentation culture medium on flocculant synthesis is investigated. The distinction lies in that the concentration of trisodium citrate in the fermentation culture medium used is 10 g $L^{-1}$.

Example 5

The culture condition is the same as that of Example 1, the effect of the composition of fermentation culture medium on flocculant synthesis is investigated. The distinction lies in that the concentration of trisodium citrate in the fermentation culture medium used is 12 g $L^{-1}$.

Example 6

The culture condition is the same as that of Example 1, the effect of the composition of fermentation culture medium on flocculant synthesis is investigated. The distinction lies in that the concentration of glycerol in the fermentation culture medium used is 10 g $L^{-1}$.

Example 7

The culture condition is the same as that of Example 1, the effect of the composition of fermentation culture medium on flocculant synthesis is investigated. The distinction lies in that the concentration of glycerol in the fermentation culture medium used is 15 g $L^{-1}$.

Example 8

The culture condition is the same as that of Example 1, the effect of the composition of fermentation culture medium on flocculant synthesis is investigated. The distinction lies in that the concentration of urea in the fermentation culture medium used is 1 g $L^{-1}$.

Example 9

The culture condition is the same as that of Example 1, the effect of the composition of fermentation culture medium on flocculant synthesis is investigated. The distinction lies in that the concentration of urea in the fermentation culture medium used is 3 g $L^{-1}$.

Example 10

The culture condition is the same as that of Example 1, the effect of the composition of fermentation culture medium on flocculant synthesis is investigated. The distinction lies in that the concentration of yeast extract in the fermentation culture medium used is 0.5 g $L^{-1}$.

Example 11

The culture condition is the same as that of Example 1, the effect of the composition of fermentation culture medium on flocculant synthesis is investigated. The distinction lies in that the concentration of yeast extract in the fermentation culture medium used is 1 g $L^{-1}$.

Example 12

The culture condition is the same as that of Example 1, the effect of the composition of fermentation culture medium on flocculant synthesis is investigated. The distinction lies in that the concentration of $NH_4Cl$ in the fermentation culture medium used is 2 g $L^{-1}$.

Example 13

The culture condition is the same as that of Example 1, the effect of the composition of fermentation culture medium on flocculant synthesis is investigated. The distinction lies in that the concentration of $NH_4Cl$ in the fermentation culture medium used is 6 g $L^{-1}$.

Example 14

The culture condition is the same as that of Example 1, the effect of the composition of fermentation culture medium on flocculant synthesis is investigated. The distinction lies in that the concentration of sodium glutamate in the fermentation culture medium used is 2 g $L^{-1}$.

Example 15

The culture condition is the same as that of Example 1, the effect of the composition of fermentation culture medium on flocculant synthesis is investigated. The distinction lies in that the concentration of sodium glutamate in the fermentation culture medium used is 6 g $L^{-1}$.

Example 16

The culture condition is the same as that of Example 1, the effect of the composition of fermentation culture medium on flocculant synthesis is investigated. The distinction lies in that the concentration of $MgSO_4$ in the fermentation culture medium used is 0.3 g $L^{-1}$.

Example 17

The culture condition is the same as that of Example 1, the effect of the composition of fermentation culture medium on flocculant synthesis is investigated. The distinction lies in that the concentration of $MgSO_4$ in the fermentation culture medium used is 0.4 g $L^{-1}$.

Example 18

The culture condition is the same as that of Example 1, the effect of the composition of fermentation culture medium on flocculant synthesis is investigated. The distinction lies in that the concentration of $K_2HPO_4$ in the fermentation culture medium used is 1.2 g $L^{-1}$.

Example 19

The culture condition is the same as that of Example 1, the effect of the composition of fermentation culture medium on flocculant synthesis is investigated. The distinction lies in that the concentration of $K_2HPO_4$ in the fermentation culture medium used is 2 g $L^{-1}$.

Example 20

The culture condition is the same as that of Example 1, the effect of the composition of fermentation culture medium on flocculant synthesis is investigated. The distinction lies in that the concentration of $KH_2PO_4$ in the fermentation culture medium used is 1 g $L^{-1}$.

Example 21

The culture condition is the same as that of Example 1, the effect of the composition of fermentation culture medium on flocculant synthesis is investigated. The distinction lies in that the concentration of $KH_2PO_4$ in the fermentation culture medium used is 3 g $L^{-1}$.

Example 22

The culture condition is the same as that of Example 1, the effect of the composition of fermentation culture medium on flocculant synthesis is investigated. The distinction lies in that the concentration of NaCl in the fermentation culture medium used is 1 g $L^{-1}$.

Example 23

The culture condition is the same as that of Example 1, the effect of the composition of fermentation culture medium on flocculant synthesis is investigated. The distinction lies in that the concentration of NaCl in the fermentation culture medium used is 3 g $L^{-1}$.

Example 24

Figure 2:
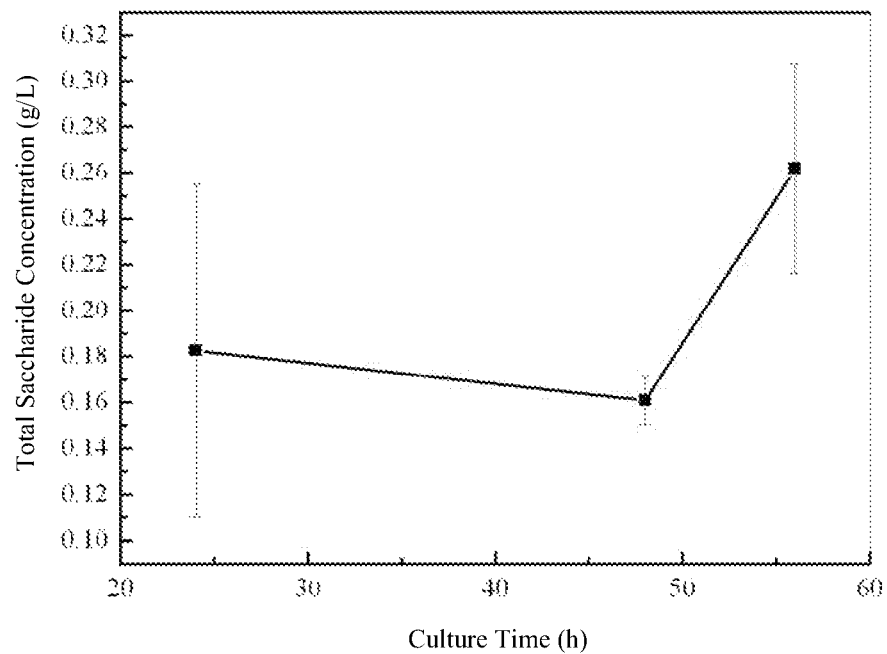
FIG. 2 is the total saccharide concentration in the flocculant determined by phenol-sulfuric acid method.

The culture condition is the same as that of Example 1, and phenol-sulfuric acid method is used to determine the content of polysaccharides in the obtained flocculant (see FIG. 2).

Example 25

The culture condition is the same as that of Example 1, and ion chromatography is used to determine γ-polyglutamic acid (γ-PGA) in the obtained flocculant.

Figure 3:
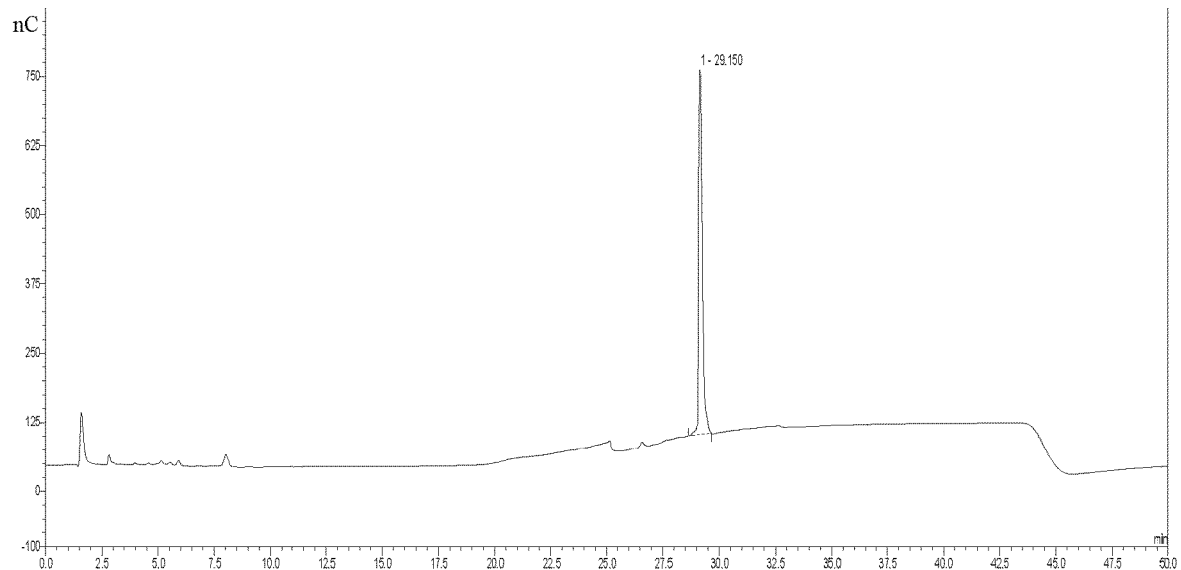
FIG. 3 is the ion chromatogram of L-Glu standard.
Figure 4:
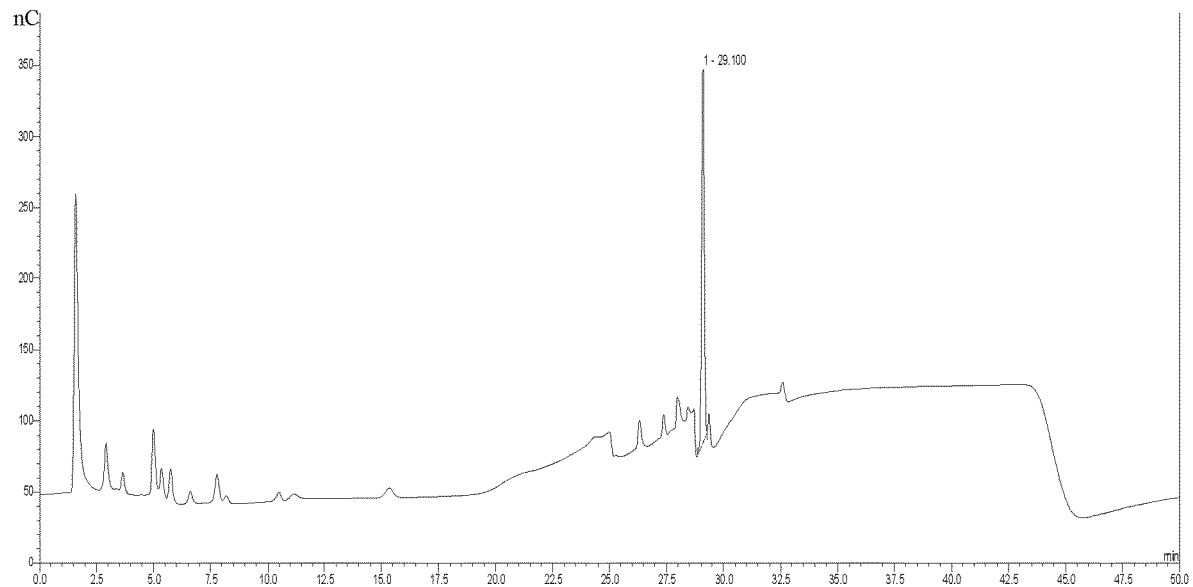
FIG. 4 is the ion chromatogram of flocculant hydrolysate.

L-Glutamic acid standard is taken as the reference, and ion chromatography is used to analyze the acidic hydrolysate of the product. As can be seen from FIGS. 3 and 4, the peak time of L-Glu standard and the hydrolysate of the product is about 29.1 min, which confirms that the fermentation product contains polypeptides composed of glutamic acid monomers.

The invention claimed is:

1. A method for simultaneously synthesizing a flocculant by using *Bacillus licheniformis*, wherein the specific steps thereof are as follows:
  1) bacterial strain activation: *Bacillus licheniformis* is inoculated to a slant medium to be cultured, wherein the composition of the slant culture medium is: yeast extract 2 g/L, beef extract 2 g/L, tryptone 5 g/L, glucose 15 g/L, $FeSO_4$ trace, agar 18 g/L and pH 5~7.5;
  2) preparation of seed: a single colony on a fresh plate is inoculated to a seed culture medium to be cultured, wherein the composition of the seed culture medium is: glucose 10 g/L, yeast extract 0.5 g/L, urea 0.5 g/L, $K_2HPO_4$ 0.1 g/L, $KH_2PO_4$ 0.1 g/L, NaCl 0.1 g/L and $MgSO_4 \cdot 7H_2O$ 0.2 g/L, and;
  3) fermentation culture: a seed fermentation broth is inoculated to a fermentation culture medium to be cultured, and then the biological flocculant with two different components is obtained, wherein the composition of the fermentation culture medium is: glucose 5~15 g/L, trisodium citrate 10~15 g/L, glycerol 10~15 g/L, urea 1~3 g/L, yeast extract 0.5~1 g/L, $NH_4Cl$ 2~6 g/L, sodium glutamate 2~6 g/L, $MgSO_4$ 0.3~0.5 g/L, $K_2HPO_4$ 0.5~2 g/L, $KH_2PO_4$ 1~5 g/L, NaCl 1~3 g/L and pH 5~7.5; and
  wherein the flocculant prepared by the method has polysaccharide and poly-γ-glutamic acid as two different active components and wherein the polysaccharide content is 26.67%-43.33% and the poly-γ-glutamic acid content is 31.63%.

2. The method for simultaneously synthesizing a flocculant by using *Bacillus licheniformis* of claim 1, wherein, in step 1), the culture condition is cultured at 37° C. and 200 r/min for 12~18 h.

3. The method for simultaneously synthesizing a flocculant by using *Bacillus licheniformis* of claim 1, wherein, in step 2), the culture condition is: temperature 37° C., the shaking speed of shaker 200 r/min, and culture time 16 h.

4. The method for simultaneously synthesizing a flocculant by using *Bacillus licheniformis* of claim 1, wherein, in step 3), the inoculation amount of the inoculation is 3%.

5. The method for simultaneously synthesizing a flocculant by using *Bacillus licheniformis* of claim 1, wherein, in step 3), the culture condition is cultured in shaking flask under the condition of 200 r/min at the temperature of 37° C., with liquid loading volume of 50 mL/250 mL, and fermentation time of 1648 h.

\* \* \* \* \*